United States Patent
Takamura et al.

(10) Patent No.: US 10,344,112 B2
(45) Date of Patent: *Jul. 9, 2019

(54) ALKYLENE OXIDE-MODIFIED DIPENTAERYTHRITOL (METH)ACRYLATE AND REACTIVE COMPOSITION CONTAINING SAME

(71) Applicant: DAI-ICHI KOGYO SEIYAKU CO., LTD., Kyoto-shi, Kyoto (JP)

(72) Inventors: Naohiro Takamura, Kyoto (JP); Masato Kameda, Kyoto (JP); Manabu Kikuta, Kyoto (JP); Teruaki Sugahara, Kyoto (JP)

(73) Assignee: DAI-ICHI KOGYO SEIYAKU CO., LTD., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/380,975

(22) PCT Filed: Feb. 19, 2013

(86) PCT No.: PCT/JP2013/053932
§ 371 (c)(1),
(2) Date: Aug. 26, 2014

(87) PCT Pub. No.: WO2013/129173
PCT Pub. Date: Sep. 6, 2013

(65) Prior Publication Data
US 2015/0038662 A1    Feb. 5, 2015

(30) Foreign Application Priority Data

Feb. 28, 2012 (JP) .................. 2012-041683

(51) Int. Cl.
  *C08F 220/28*  (2006.01)
  *C07C 69/54*   (2006.01)
  *C08F 222/10*  (2006.01)

(52) U.S. Cl.
  CPC ............ *C08F 220/28* (2013.01); *C07C 69/54* (2013.01); *C08F 222/1006* (2013.01); *C08F 2220/286* (2013.01); *C08F 2220/287* (2013.01)

(58) Field of Classification Search
  CPC ... C08F 220/28; C08F 222/1006; C07C 69/54
  See application file for complete search history.

(56) References Cited

U.S. PATENT DOCUMENTS

2010/0081070 A1* 4/2010 Taguchi .............. C08K 5/0041
                                                        430/7

FOREIGN PATENT DOCUMENTS

| JP | 59-84844   | 5/1984 |
| JP | 62-61049   | 3/1987 |
| JP | 62-178542  | 8/1987 |
| JP | 2-10136    | 1/1990 |
| JP | 4-89872    | 3/1992 |
| JP | 10-062986  | 3/1998 |
| JP | 2003-167339| 6/2003 |
| JP | 2010-113244| 5/2010 |

(Continued)

OTHER PUBLICATIONS

Extended European Search Report dated Sep. 8, 2015 in corresponding European Application No. 13754689.1.
CAS: 1228636-21-2, 2-Propenoic Acid, Jun. 30, 2010.
Third Party's Submission, dated Mar. 24, 2015, in corresponding Japanese Appln. No. 2012-041683, and partial English translation thereof.

(Continued)

*Primary Examiner* — Karuna P Reddy
(74) *Attorney, Agent, or Firm* — Wenderoth, Lind & Ponack, L.L.P.

(57) ABSTRACT

An alkylene oxide-modified polyfunctional (meth)acrylate is provided wherein the problems according to high crystallinity or high viscosity are improved, and the photosensitivity, etc. is enhanced. The compound has a structure represented by the following formula (I), provided that in the formula (I), R represents a substituent represented by the formula (II); AO represents one member or two or more members selected from alkylene oxide units represented by —$CH_2CH_2O$—, —$CH_2CH(CH_3)O$—, —$CH_2CH_2CH_2CH_2O$— and —$CH_2CH(C_2H_5)O$—; l indicating the average polymerization degree of the added alkylene oxide is $0 < l \leq 5$; the average value of m is more than 0 and 6 or less; each of the average values of n and o is from 0 to 6, the total value of m, n and o is 6, and in the formula (II), $R^2$ represents a hydrogen atom or a methyl group.

[Chem. 1]

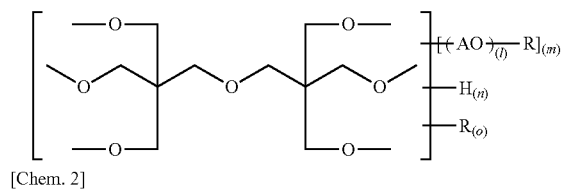

(I)

[Chem. 2]

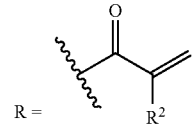

(II)

1 Claim, No Drawings

(56) References Cited

FOREIGN PATENT DOCUMENTS

| | | |
|---|---|---|
| JP | 2010-128328 | 6/2010 |
| JP | 2011-180478 | 9/2011 |
| JP | 2012-48202 | 3/2012 |

OTHER PUBLICATIONS

Chinese Office Action, dated Mar. 20, 2015, in corresponding Chinese Appln. No. 201380011546.0, and partial English translation thereof.
International Search Report for PCT/JP2013/053932, dated May 21, 2013.
Japanese Notification of Reasons for Refusal, dated Apr. 28, 2015, in corresponding Japanese Appln. No. 2012-041683, and English translation thereof.
Communication pursuant to Article 94(3) EPC dated Nov. 14, 2017 in European Application No. 13 754 689.1.
Communication pursuant to Article 94(3) EPC dated Apr. 3, 2019 in European Patent Application No. 13 754 689.1.

* cited by examiner

ALKYLENE OXIDE-MODIFIED DIPENTAERYTHRITOL (METH)ACRYLATE AND REACTIVE COMPOSITION CONTAINING SAME

TECHNICAL FIELD

The present invention relates to an alkylene oxide-modified dipentaerythritol (meth)acrylate, that is, an alkylene oxide-modified dipentaerythritol (meth)acrylate having low viscosity, low crystallinity and high photosensitivity and exhibiting little cure shrinkage and high hardness after curing, and a reactive composition containing the same in comparison with conventional polyfunctional (meth)acrylate.

BACKGROUND ART

In a reactive composition, (meth)acrylic acid esters are one important component of monomers for copolymerization and are blended for a variety of diversified purposes/applications. However, polyfunctional monomers generally added as a crosslinking component intrinsically exhibit crystallinity at room temperature or a temperature lower than that or are a compound having very high viscosity. Therefore, the viscosity of the reactive composition as a whole is often increased and handling becomes difficult.

For example, in a coating application such as hard coating or in an ink composition for inkjet printing, a (meth)acrylate of a polyfunctional alcohol represented by a pentaerythritol such as tripentaerythritol, dipentaerythritol, ditrimethylolpropane and diglycerin, and a polymerization product of trimethylolpropane, glycerin, etc. must be blended so as to impart mechanical strength or chemical stability to the reactive composition after curing. However, since the polyfunctional (meth)acrylate such as, dipentaerythritol (meth)acrylate used in the above-described reactive composition for general purposes has very high viscosity in itself and causes a great increase in the viscosity of the reactive composition, dilution with an organic solvent is required, which is not preferable also in view of VOC regulations. Furthermore, in the application such as film coating, the polyfunctional (meth)acrylate raises a problem that the film coated is curled (warped) due to cure shrinkage.

In other applications such as a resin composition for dry film resist, color resist or black resist, in addition to the requirement for film physical properties after curing, it is required to complete the curing even with a low exposure amount, that is, exhibit high sensitivity, at the time of curing with an active energy ray such as ultraviolet ray and electron beam. Above all, in a highly light-shielding composition wherein a pigment or a dye is blended at a high concentration, such as color resist and black resist, the utility value of a material capable of curing even with a low exposure amount may be extremely high.

As described above, the conventionally used (meth)acrylate of a polyfunctional alcohol has mechanical properties expected for the polyfunctional structure as well as undesired properties such as high viscosity, high crystallinity and high cure shrinkage.

As means to improve this problem, an alkylene oxide-modified polyfunctional alcohol, for example, an ethylene oxide-modified acrylate of dipentaerythritol, has been recently launched on the market. Although a compound where a long-chain alkylene oxide having an addition mol number exceeding 5 mol/hydroxyl group is introduced can achieve reduction in the viscosity or crystallinity, the original mechanical strength expected for the polyfunctional structure cannot be maintained due to decrease in the crosslinking density. However, it is known that the above-described defect of the conventional alkylene oxide-unmodified polyfunctional (meth)acrylate cannot be improved only by merely decreasing the addition mol number.

The inventors of the present invention have found that the problem above can be solved by optimizing the alkylene oxide addition mol number of an alkylene oxide-modified dipentaerythritol (meth)acrylate and controlling the content of a poly(alkylene oxide) (meth)acrylate occurring as a by-product in the alkylene oxide addition reaction.

In this connection, although Patent Document 1 refers to the amount of an ethylene oxide derivative occurring as a by-product in an ethylene oxide-modified dipentaerythritol, only the effluent and taste are evaluated and it is preferable that the amount of the by-product is 0.5% by mass or less, which differs from the present invention in both the object and the constitution.

Also, although Patent Document 2 refers to the alkylene oxide addition mol number and physical properties for dipentaerythritol, in Examples, only a propylene oxide derivative is shown and as for the physical properties, only the viscosity is evaluated, where the viscosity is at a level which is not enough to solve the above-described problem.

PRIOR ART LITERATURE

Patent Document

Patent Document 1: JP-A-62-178542
Patent Document 2: JP-A-2-10136

SUMMARY OF THE INVENTION

Problems that the Invention is to Solve

Under these circumstances, the present invention has been made, and an object of the present invention is to provide an alkylene oxide-modified polyfunctional (meth)acrylate compound which improves the problems such as bad handleability and high cure shrinkage rate according to high crystallinity or high viscosity of a polyfunctional (meth)acrylate added to a reactive composition, and has enhanced photosensitivity, surface hardness, contamination resistance, etc., and a reactive composition containing the same.

Means for Solving the Problems

The inventors of the present invention have carried out intensive studies and found that when an alkylene oxide-modified dipentaerythritol (meth)acrylate having a specific structure contains a specific amount of a poly(alkylene oxide) (meth)acrylate, the compound exhibits excellent photosensitivity, low crystallinity, low viscosity and low cure shrinkage and the cured product thereof has high hardness, in comparison with a (meth)acrylate of a polyfunctional alcohol represented by dipentaerythritol, pentaerythritol, ditrimethylolpropane, trimethylolpropane, pentaerythritol, etc., by which the present invention was accomplished.

Namely, an alkylene oxide-modified dipentaerythritol (meth)acrylate (which may be referred as merely "the compound of the present invention") has a structure represented by the following formula (I):
provided that in the formula (I), R represents a substituent represented by the formula (II); AO represents one member or two or more members selected from alkylene oxide units represented by —CH$_2$CH$_2$O—, —CH$_2$CH(CH$_3$)O—, —CH$_2$CH$_2$CH$_2$CH$_2$O— and —CH$_2$CH(C$_2$H$_5$)O—; l indicating the average polymerization degree of the added alkylene oxide is 0<l≤5; the average value of m is more than 0 and 6 or less; each of the average values of n and o is from 0 to 6; the total value of m, n and o is 6; and in the formula (II), R$^2$ represents a hydrogen atom or a methyl group:

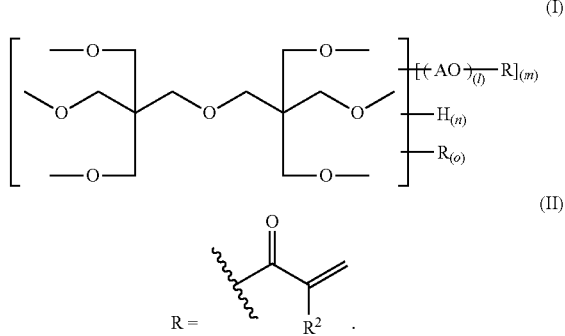

A reactive composition of the present invention contains the above alkylene oxide-modified dipentaerythritol (meth)acrylate of the present invention and a poly(alkylene oxide) (meth)acrylate.

In the above reactive composition, it is preferable the content of said alkylene oxide-modified dipentaerythritol (meth)acrylate is 80% by mass or more and less than 100% by mass and the content of the poly(alkylene oxide) (meth)acrylate is more than 0% by mass and 20% by mass or less.

Effect of the Invention

The alkylene oxide-modified dipentaerythritol (meth)acrylate compound represented by the formula (1) of the present invention, wherein the alkylene oxide addition mol number is optimized, has excellent photosensitivity, low crystallinity, low viscosity and low cure shrinkage by controlling the content of a (meth)acrylate of an alkylene oxide polymer, and the cured product thereof has high hardness, so that a polymerizable resin composition in which a (meth)acrylate of a polyfunctional alcohol represented by dipentaerythritol, pentaerythritol, ditrimethylolpropane, trimethylolpropane, pentaerythritol and the like has been conventionally blended can be more decreased in the viscosity and the physical properties of the cured product can be enhanced.

Also, according to the above-described characteristics, particularly in a reactive composition of a solventless type, a monofunctional monomer added for the purpose of viscosity reduction/viscosity adjustment need not be decreased in its content or need not be added, so that the concentration of a (meth)acryloyl group as a polymerizable functional group in the reactive composition can be increased.

As a result, the curability can be enhanced, that is, a cured product having a high crosslinking density can be obtained, so that in addition to the mechanical properties such as scratch resistance, the contamination resistance, solvent resistance and heat resistance can be improved. As for the usage, the cured product can be suitably used for a heat-sensitive recording material, an optical disk, an optical sheet, an inkjet ink, an ink for dampening water-free printing (e.g., ink for flexographic printing, ink for screen printing), an optical fiber, etc. On the other hand, a reactive composition of a solvent type including a water system enjoys enhanced curability and enhanced adherence to a substrate owing to reduction in cure shrinkage and allows for no progress of crosslinking by heat because of a small amount of a residual double bond in the cured coating film, whereby, for example, no deterioration of the adherence in a heat resistance test or improvement of weather resistance or light resistance is achieved.

Accordingly, the compound and reactive composition of the present invention can be said to be a material having a remarkably great superiority in the usage, e.g., a reactive composition for coating such as hard coating, a reactive composition for an ink of inkjet printing, etc., a reactive composition for a resist such as color resist, and a film coating etc.

In addition, although the compound and reactive composition of the present invention can exert the above-described properties by the single use thereof, they can exert their properties even in use in combination with an existing reactive composition, for example, a alkylene oxide-unmodified polyfunctional (meth)acrylate such as acylate of dipentaerythritol, and thus can also be utilized as an additive.

MODE FOR CARRYING OUT THE INVENTION

<Alkylene Oxide-Modified Dipentaerythritol (Meth)acrylate>

The compound of the present invention has a structure represented by the formula (I). In the formula (I), AO represents any one alkylene oxide unit represented by —CH$_2$CH$_2$O—, —CH$_2$CH(CH$_3$)O—, —CH$_2$CH$_2$CH$_2$CH$_2$O— or —CH$_2$CH(C$_2$H$_5$)O—, that is, ethylene oxide, propylene oxide or butylene oxide, and ethylene oxide is preferable in view of viscosity, photosensitivity and polymerization ratio. One of these alkylene oxide units may be present alone, or two or more thereof may be present in combination.

l indicating the average polymerization degree of the added alkylene oxide is 0<l≤5, preferably 0<l≤2. Also, the average value of m is more than 0 and 6 or less, preferably from 2 to 6. The average value of n is from 0 to 6, preferably from 0 to 2. The average value of o is from 0 to 6, preferably from 0 to 4. The total value of m, n and o is 6.

R is a (meth)acryloyl group represented by the formula (II). In the formula (2), R$^2$ is a hydrogen atom or a methyl group, and the wavy line part indicates a bonding moiety.

Namely, the compound of the present invention has a structure where 6 hydroxyl groups of dipentaerythritol are partially or entirely converted into a (meth)acrylic acid ester group represented by the formula (II) through a spacer composed of ethylene oxide, propylene oxide, butylene oxide or a plurality of members thereof.

<Production Method of Alkylene Oxide-Modified Dipentaerythritol (Meth)Acrylate>

Although the alkylene oxide-modified polyfunctional (meth)acrylate of the present invention can be produced, for example, by the following method, the production route is not particularly limited, and any production method may be used.

The method for alkylene oxide modification using dipentaerythritol as a raw material may be arbitrarily selected. The general technique includes a method using a cyclic carbonate such as ethylene carbonate, propylene carbonate and butylene carbonate, and a method using ethylene chlorohydrin, in addition to a method using an alkylene oxide such as ethylene oxide, propylene oxide and butylene oxide.

In the production method described below, since the compound of the present invention and the (meth)acrylic acid compound used as a raw material have high polymerizability, a polymerization inhibitor may be appropriately used so as to prevent the polymerization from progressing at the time of production or during storage of the product. The polymerization inhibitor includes hydroquinones such as p-benzoquinone, hydroquinone, hydroquinone monomethyl ether and 2,5-diphenyl-para-benzoquinone, N-oxyradicals such as tetramethylpiperidinyl-N-oxyradical (TEMPO), substituted catechols such as tert-butyl catechol, amines such as phenothiazine, diphenylamine and phenyl-β-naphthylamine, cupferron, nitrosobenzene, picric acid, molecular oxygen, sulfur, copper(II) chloride, and the like. Among these, hydroquinones, phenothiazine and N-oxyradicals are preferable in view of general versatility and polymerization inhibitory effect.

The amount of the polymerization inhibitor added has a lower limit of approximately 10 ppm or more, preferably 30 ppm or more, and usually an upper limit of 5,000 ppm or less, preferably 1,000 ppm or less, based on the compound represented by the formula (I) that is the object. If the amount added is too small, a polymerization inhibitory effect is not sufficiently exerted, which leads to a risk that the polymerization may proceed at the time of production or during storage of the product, whereas if the amount added is too large, the curing/polymerization reaction may be conversely inhibited, which is disadvantageous in that when the compound of the present invention is used alone or formed into a polymerizable resin composition, a decrease in photosensitivity, a crosslinking failure of the cured product, or deterioration of physical properties such as mechanical strength may be caused.

The general method for introducing a (meth)acrylic acid ester group in producing the compound of the present invention includes, for example, a transesterification method using a (meth)acrylic acid ester corresponding to the objective structure, such as methyl acrylate and methyl methacrylate; an acid chloride method using a (meth)acrylic acid chloride; a method using a condensing agent such as N,N'-dicyclohexylcarbodiimide, 2-chloro-1,3-dimethylimidazolium chloride, propanephosphonic anhydride, carbonyldiimidazole (CDI) and WSCD (water-soluble carbodiimide); and a dehydration and esterification method of performing azeotropic dehydration with a (meth)acrylic acid in the presence of an acid catalyst. In the following, with respect to a representative esterification reaction of an alkylene oxide-modified dipentaerythritol, possible conditions for production are described.

The reaction of a (meth)acrylic acid and an alkylene oxide-modified dipentaerythritol may be performed in the presence of an acid catalyst with distilling off the water produced. As for the acid used, an acid employed for an ordinary esterification reaction can be used without any particular limitation. Examples thereof include an inorganic acid such as sulfuric acid and hydrochloric acid, an organic sulfonic acid such as p-toluenesulfonic acid, methanesulfonic acid and camphorsulfonic acid, an acid-type ion exchange resin, a Lewis acid such as fluorinated boron•ether complex, and a water-soluble Lewis acid such as lanthanide triflate. One of these acids may be used alone, or two or more arbitrary acids thereof may be mixed and used.

As for the amount of the acid used, the lower limit is 0.1 mol equivalents or more, preferably from 0.5 mol equivalents or more, based on the alkylene oxide-modified dipentaerythritol that is the substrate. On the other hand, although the upper limit is not limited, it is usually 20 mol equivalents or less, preferably from 10 mol equivalents or less. If the amount of the acid catalyst is too small, the reaction may disadvantageously proceed slowly or stop, whereas if the amount used is too large, there is a tendency that a problem such as coloration of the product or remaining of the catalyst may arise or an undesired side reaction such as production of a Michael adduct may occur.

Although the reaction may be performed in either a solvent system or a solventless system, in view of production of a by-product and handling in the process, a solvent system is preferable. In the case of using a solvent, although the solvent used is not limited, for example, an aromatic hydrocarbon solvent such as toluene and xylene, an aliphatic hydrocarbon solvent such as hexane and heptane, an ether-based solvent such as diethyl ether, tetrahydrofuran, monoethylene glycol dimethyl ether and diethylene glycol dimethyl ether, and a halogen-based solvent such as methylene chloride, chloroform and carbon tetrachloride, are suitably used. One of these solvents may be used alone, or a plurality of arbitrary solvents thereof may be mixed and used.

In the case of using a solvent, the amount thereof is, in terms of the concentration of the alkylene oxide-modified pentaerythritol as the raw material, usually from 1% by mass or more, preferably from 20% by mass or more. Although the upper limit is not particularly limited, it is usually from 80% by mass or less, preferably from 70% by mass or less. The reaction is performed usually at a temperature not less than the boiling point of the solvent used, with distilling off the water produced. However, in the case of performing a reaction using the above-described (meth)acrylic acid chloride or condensing agent, the reaction is sometimes performed at a temperature not more than the boiling point of the solvent or under ice cooling. Although the reaction time is arbitrarily selected, the end point of the reaction can be recognized by measuring the amount of water produced or the acid value in the system.

As for the reaction time, the lower limit is usually from 30 minutes or more, preferably from 60 minutes or more, and the upper limit is not particularly limited and is usually from 20 hours or less, preferably from 10 hours or less.

<Purification Method>

The compound represented by the formula (I) produced by the above-described reaction can be purified by a conventionally used purification method without any particular limitation. Examples thereof include a distillation method, a recrystallization method, an extraction washing method, and an adsorption treatment method. In the case of performing distillation, the mode thereof may be arbitrarily selected from simple distillation, rectification, thin-film distillation, molecular distillation, and the like.

<Storage Method of (Meth)Acrylic Acid Ester Monomer>

Since the (meth)acrylic acid ester monomer of the present invention has polymerizability, it is preferably stored in a cold dark place. In addition, it is also possible to store the compound by using the above-described polymerization inhibitor in the above-described amount for preventing polymerization.

<Reactive Composition>

The reactive composition of the present invention contains, as described above, the alkylene oxide-modified dipentaerythritol (meth)acrylate of the present invention and a poly(alkylene oxide) (meth)acrylate. Here, as the poly (alkylene oxide) (meth)acrylate, a by-product in the production of the alkylene oxide-modified dipentaerythritol (meth) acrylate can be directly utilized without isolating it, and specific examples of the polymerized alkylene oxide include those having a polymerization degree of 1 to 9, such as polyethylene glycol, polypropylene glycol and polybutylene glycol.

In the reactive composition of the present invention, the content of the alkylene oxide-modified dipentaerythritol (meth)acrylate is from 80% by mass to less than 100% by mass, and the content of the poly(alkylene oxide) (meth) acrylate is preferably from more than 0% by mass and 20% by mass or less, more preferably from 12% by mass or less. If the content of the poly(alkylene oxide) (meth)acrylate exceeds 20% by mass, this may cause a rise in the viscosity or lead to a deterioration in hardness, abrasion property, contamination resistance, acid resistance, alkali resistance, water resistance, alkali resistance and chemical resistance of the cured product.

The polymerization/curing of the reactive composition of the present invention can be performed by a generally known method, and the method is not particularly limited. For example, a method of polymerizing the composition in the presence of a radical initiator, a method of polymerizing the composition by an ultraviolet ray emitted from a light source such as LED and high-pressure mercury lamp or by an active energy ray using an electron beam, a thermal polymerization method, and a method such as anionic polymerization and addition polymerization, may be used individually or in combination.

Although the polymerization initiator is not particularly limited, as the photopolymerization initiator, for example, aromatic ketones such as benzophenone etc., an aromatic compound such as anthracene and α-chloromethylnaphthalene etc., and a sulfur compound such as diphenyl sulfide and thiocarbamate etc., can be used.

As the radical polymerization initiator, for example, an organic peroxide such as benzoyl peroxide, methylcyclohexanone peroxide, cumene hydroperoxide, diisopropylbenzene peroxide, di-tert-butyl peroxide, tert-butyl peroxybenzoate, diisopropyl peroxycarbonate and tert-butyl peroxyisopropylmonocarbonate, and an azo compound such as 2,2'-azobisisobutyronitrile (AIBN), can be used. If desired, such a photopolymerization initiator and a radical polymerization initiator may be used in combination.

The polymerization initiator for the polymerization by an active energy ray such as ultraviolet ray includes, for example, acetophenone, acetophenone benzyl ketal, 1-hydroxycyclohexyl phenyl ketone, 2,2-dimethoxy-1,2-diphenylethan-1-one, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethyl ether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholino-propan-1-one, 2-benzyl-2-dimethylamino-1-(4-morpholinophenyl)-butanone-1,4-(2-hydroxyethoxy) phenyl-(2-hydroxy-2-propyl)ketone, 2,4,6-trimethylbenzoyldiphenylphosphine oxide, bis-(2,6-dimethoxybenzoyl)-2,4,4-trimethylpentylphosphine oxide, and oligo(2-hydroxy-2-methyl-1-(4-(1-methylvinyl)phenyl) propanone) etc.

In this connection, the commercial product of the polymerization initiator for polymerization by an active energy ray includes, for example, Irgacure 184, 369, 651, 500, 819, 907, 784, 2959, CGI1700, CGI1750, CGI1850, CG24-61, Darocur 1116, 1173 (trade names) produced by Ciba Specialty Chemicals); Lucirin TPO (trade name) produced by BASF; Ubecryl P36 (trade name) produced by UCB; and Ezacure KIP150, KIP65LT, KIP100F, KT37, KT55, KT046, KIP75/B (trade names) produced by Fratelli Lamberti.

The amount used of the above-described photopolymerization initiator, radical polymerization initiator or polymerization initiator for polymerization by an active energy ray may be selected according to a known polymerization reaction. For example, the radical polymerization initiator is suitably used in an amount of usually from 0.0001 to 10 parts by weight, preferably from 0.001 to 5 parts by weight, based on the compound represented by the formula (I) of the present invention. As for the reaction temperature, the lower limit is usually from 0° C. or more, preferably from 10° C. or more, and the upper limit is usually from 200° C. or less, preferably from 100° C. or less.

EXAMPLES

Although the present invention is described in more detail below by referring to Examples, the present invention is not limited to the following Examples as long as it is included in the gist. In this connection, unless otherwise indicated, "%" is % by mass, and "parts" is on the mass basis.
<Conditions of Liquid Chromatography Mass Spectrometry (Hereinafter, Simply Referred to as LC-MS Analysis)>

The LC-MS analysis in Examples and Comparative Examples was performed under the following conditions.
[LC Portion]
1100 Series manufactured by Agilent Technologies
Column: Inertsil ODS-2 (4.6 mm φ×250 mm, 5 μm), eluent: water 80.0%-30 min→0.0%, methanol 20.0%-30 min→100.0%, column temperature: 40° C., flow rate: 1 mL/min, injection amount: 5 μL (200 ppm methanol solution), detector: UV, RI
[MS Portion]
JMS T100LP (manufactured by JEOL)
Ring lens voltage: 10 V, ionization process: APCl+, temperature of solvent removal chamber: 350° C., needle voltage: 2,500 V, orifice 1 temperature: 80° C., orifice 1 voltage: 60 V, voltage between ion guide peaks: 1,000 V, orifice 2 voltage: 5 V.
<Hydroxyl Value Measurement Conditions>

Acetic acid and pyridine were mixed in a weight ratio of 1:9 and used as an acetylation reagent. A sample is weighed in a flask; added with the acetylation reagent; and heated at 80° C. for 2 hours. After the reaction, titration was performed with an aqueous 1 mol/l potassium hydroxide solution by using phenolphthalein as an indicator.
<NMR Analysis>

As for the results of NMR analysis, the attribution of each peak is indicated by the number ((1) to (3)) shown in the following formula.

[Chem. 3]

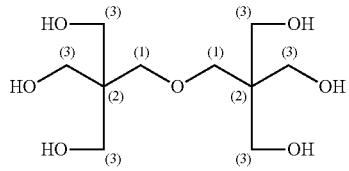

Example 1

(Synthesis of Dipentaerythritol 2EO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 132 g (3 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 2EO adduct was 982.

Subsequently, 343 g (1 mol) of the obtained ethylene glycol-modified dipentaerythritol (OH value: 982), 562 g (7.8 mol) of acrylic acid, 45 g of para-toluenesulfonic acid, 900 g of toluene and 0.9 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 112 g. After the reaction, aqueous alkali washing and water washing were preformed to separate the upper-layer toluene layer, and the toluene was removed by distillation under reduced pressure to obtain 594 g (yield: 89%) of dipentaerythritol 2EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 2EO adduct acrylate. The results of NMR analysis and LC-MS analysis are shown below, and the attribution of peak of NMR is indicated by the above-described number.

<Dipentaerythritol 2EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 2EO Adduct Acrylate> ($^1$H-NMR Analysis (400 MHz), in CDCl3)

From 3.3 to 4.1 ppm (16H): derived from (1) and (3), from 3.6 to 4.4 ppm (8H): derived from ethylene oxide added to OH of (3), from 5.7 to 6.4 ppm (18H): derived from double bond of acrylic acid ester, and 7.3 ppm: derived from deuterated chloroform.

<Dipentaerythritol 2EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 2

(Synthesis of Dipentaerythritol 3EO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 176 g (4 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 3EO adduct was 897.

Subsequently, 375 g (1 mol) of the obtained ethylene glycol-modified dipentaerythritol (OH value: 897), 562 g (7.8 mol) of acrylic acid, 46 g of para-toluenesulfonic acid, 900 g of toluene and 0.9 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 112 g. After the reaction, aqueous alkali washing and water washing were preformed to separate the upper-layer toluene layer, and the toluene was removed by distillation under reduced pressure to obtain 615 g (yield: 88%) of dipentaerythritol 3EO adduct acrylate represented by the formula (I).

With respect to this product, measurement of hydroxyl value and analyses by $^1$H-NMR, $^{13}$C-NMR, HPLC and LC-MS were performed, as a result, the compound obtained was revealed to be dipentaerythritol 3EO adduct acrylate. The results of NMR analysis and LC-MS analysis are shown below, and the attribution of peak of NMR is indicated by the above-described number.

<Dipentaerythritol 3EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 3EO Adduct Acrylate> ($^1$H-NMR Analysis (400 MHz), in CDCl3)

From 3.3 to 4.1 ppm (16H): derived from (1) and (3), from 3.6 to 4.4 ppm (12H): derived from ethylene oxide added to OH of (3), from 5.7 to 6.4 ppm (18H): derived from double bond of acrylic acid ester, and 7.3 ppm: derived from deuterated chloroform.

<Dipentaerythritol 3EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 3

(Synthesis of Dipentaerythritol 3.5EO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated to 130° C., and 198 g (4.5 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 3EO adduct was 819.

Subsequently, 411 g (1 mol) of the obtained ethylene glycol-modified dipentaerythritol (OH value: 819), 562 g (7.8 mol) of acrylic acid, 48 g of para-toluenesulfonic acid, 900 g of toluene and 0.9 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 646 g (yield: 88%) of dipentaerythritol 3.5EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 3.5EO adduct acrylate. The results of NMR analysis and LC-MS analysis are shown below, and the attribution of peak of NMR is indicated by the above-described number.

<Dipentaerythritol 3.5EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 3.5EO Adduct Acrylate> ($^1$H-NMR Analysis (400 MHz), in CDCl3)

From 3.3 to 4.1 ppm (16H): derived from (1) and (3), from 3.6 to 4.4 ppm (14H): derived from ethylene oxide added to OH of (3), from 5.7 to 6.4 ppm (18H): derived from double bond of acrylic acid ester, and 7.3 ppm: derived from deuterated chloroform.

<Dipentaerythritol 3.5EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 4

(Synthesis of Dipentaerythritol 4EO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 220 g (5 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 4EO adduct was 765.

Subsequently, 440 g (1 mol) of the obtained ethylene glycol-modified dipentaerythritol (OH value: 765), 562 g (7.8 mol) of acrylic acid, 50 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 665 g (yield: 87%) of dipentaerythritol 4EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 4EO adduct acrylate. The results of NMR analysis and LC-MS analysis are shown below, and the attribution of peak of NMR is indicated by the above-described number.

<Dipentaerythritol 4EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 4EO Adduct Acrylate> ($^1$H-NMR Analysis (400 MHz), in CDCl3)

From 3.3 to 4.1 ppm (16H): derived from (1) and (3), from 3.6 to 4.4 ppm (16H): derived from ethylene oxide added to OH of (3), from 5.7 to 6.4 ppm (18H): derived from double bond of acrylic acid ester, and 7.3 ppm: derived from deuterated chloroform.

<Dipentaerythritol 4EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 5

Synthesis of Dipentaerythritol 5EO Adduct Acrylate

Into a 1 L-volume autoclave equipped with a stirring device, 254 g (1.0 mol) of dipentaerythritol (produced by Koei Chemical Co., Ltd., OH value: 1,324), 36 g of distilled water and 0.3 g of KOH were charged, and the contents were subjected to a temperature rise to 90° C. with stirring to form a slurry-like liquid. The liquid was then heated at 130° C., and 264 g (6 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 5EO adduct was 706.

Subsequently, 477 g (1 mol) of the obtained ethylene glycol-modified dipentaerythritol (OH value: 706), 562 g (7.8 mol) of acrylic acid, 52 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 697 g (yield: 87%) of dipentaerythritol 5EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 5EO adduct acrylate. The results of NMR analysis and LC-MS analysis are shown below, and the attribution of peak of NMR is indicated by the above-described number.

<Dipentaerythritol 5EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 5EO Adduct Acrylate> ($^1$H-NMR Analysis (400 MHz), in CDCl3)

From 3.3 to 4.1 ppm (16H): derived from (1) and (3), from 3.6 to 4.4 ppm (20H): derived from ethylene oxide added to OH of (3), from 5.7 to 6.4 ppm (18H): derived from double bond of acrylic acid ester, and 7.3 ppm: derived from deuterated chloroform.

<Dipentaerythritol 5EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 6

(Synthesis of Dipentaerythritol 6EO Adduct Acrylate)

Into a 1 L-volume autoclave equipped with a stirring device, 254 g (1.0 mol) of dipentaerythritol (produced by Koei Chemical Co., Ltd., OH value: 1,324), 36 g of distilled water and 0.3 g of KOH were charged, and the contents were subjected to a temperature rise to 90° C. with stirring to form a slurry-like liquid. The liquid was then heated at 130° C., and 352 g (8 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 6EO adduct was 646.

Subsequently, 521 g (1 mol) of the obtained ethylene glycol-modified dipentaerythritol (OH value: 646), 562 g (7.8 mol) of acrylic acid, 54 g of para-toluenesulfonic acid, 900 g of toluene and 1.1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 727 g (yield: 86%) of dipentaerythritol 6EO adduct acrylate represented by formula (I).

With respect to this product, measurement of hydroxyl value and analyses by $^1$H-NMR, $^{13}$C-NMR, HPLC and LC-MS were performed, as a result, the compound obtained was revealed to be dipentaerythritol 6EO adduct acrylate. The results of NMR analysis and LC-MS analysis are shown below, and the attribution of peak of NMR is indicated by the above-described number.

<Dipentaerythritol 6EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 6EO Adduct Acrylate> ($^1$H-NMR Analysis (400 MHz), in CDCl3)

From 3.3 to 4.1 ppm (16H): derived from (1) and (3), from 3.6 to 4.4 ppm (24H): derived from ethylene oxide added to OH of (3), from 5.7 to 6.4 ppm (18H): derived from double bond of acrylic acid ester, and 7.3 ppm: derived from deuterated chloroform.

<Dipentaerythritol 6EO Adduct Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 7

(Synthesis of Dipentaerythritol 4EO Adduct Acrylate with Decreased Amount of by-Product Poly(Ethylene Oxide) Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 198 g (4.5 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 4EO adduct was 765.

Subsequently, 433 g (1 mol) of the obtained ethylene glycol-modified dipentaerythritol (OH value: 778), 562 g (7.8 mol) of acrylic acid, 50 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 659 g (yield: 87%) of dipentaerythritol 4EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 4EO adduct acrylate decreased in the amount of the by-product ethylene oxide derivative. The results of NMR analysis and LC-MS analysis are shown below, and the attribution of peak of NMR is indicated by the above-described number.

<Dipentaerythritol 4EO Adduct Acrylate with Decreased By-Product Poly(Ethylene Oxide) Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 4EO Adduct Acrylate with Decreased By-product Poly(Ethylene Oxide) Acrylate> ($^1$H-NMR Analysis (400 MHz), in CDCl3)

From 3.3 to 4.1 ppm (16H): derived from (1) and (3), from 3.6 to 4.4 ppm (24H): derived from ethylene oxide added to OH of (3), from 5.7 to 6.4 ppm (18H): derived from double bond of acrylic acid ester, and 7.3 ppm: derived from deuterated chloroform.

<Dipentaerythritol 4EO Adduct Acrylate with Decreased By-Product Poly(Ethylene Oxide) Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Example 8

(Synthesis of Dipentaerythritol 4PO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.5 g of KOH were charged, and the contents were subjected to a temperature rise to 90° C. with stirring to form a slurry-like liquid. The liquid was then heated to 140° C., and 290 g (5 mol) of propylene oxide was gradually introduced into the autoclave and reacted. Along with the introduction of propylene oxide, the temperature in the autoclave was raised. Cooling was applied as needed to keep the reaction temperature at 150° C. or less. After the reaction, the pressure was reduced at 150° C. to 10 mmHg mercury column or less to remove excess propylene oxide and an propylene glycol polymer occurring as a by-product. The pH was adjusted to a value of 6 to 7 by performing neutralization with acetic acid. The OH value of the obtained dipentaerythritol 4PO adduct was 727.

Subsequently, 463 g (1 mol) of the obtained propylene glycol-modified dipentaerythritol (OH value: 567), 562 g (7.8 mol) of acrylic acid, 58 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 669 g (yield: 85%) of dipentaerythritol 4PO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 4PO adduct acrylate. The results of NMR analysis and LC-MS analysis are shown below, and the attribution of peak of NMR is indicated by the above-described number.

<Dipentaerythritol 4PO Adduct Acrylate> ($^{13}$C-NMR Analysis (400 MHz), in CDCl3)

20 ppm: derived from propylene oxide, 45 ppm: derived from (2), 60 ppm: derived from (3), from 61 to 63 ppm: derived from (3) added with propylene oxide, from 65 to 80 ppm: derived from propylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 4PO Adduct Acrylate> ($^1$H-NMR Analysis (400 MHz), in CDCl3)

1.4 ppm (12H): derived from methyl group of propylene oxide added to OH of (3), from 3.2 to 4.5 ppm (28H): derived from (I), (3) and propylene oxide (excluding methyl group) added to (3), from 5.7 to 6.5 ppm (18H): derived from (3) and acrylic acid ester bound to propylene oxide added to (3), and 7.3 ppm: derived from deuterated chloroform.

<Dipentaerythritol 4PO Adduct Acrylate> (LC-MS Analysis)

From 14 to 15 minutes: dipentaerythritol pentaacrylate and dipentaerythritol hexaacrylate, from 16.1 to 21.1: dipentaerythritol propylene oxide-modified hexaacrylate, and from 15 to 19.5 minutes: poly(propylene oxide) diacrylate.

Example 9

(Synthesis of Dipentaerythritol 6PO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.5 g of KOH were charged, and the contents were subjected to a temperature rise to 90° C. with stirring to form a slurry-like liquid. The liquid was then heated at 140° C., and 406 g (7 mol) of propylene oxide was gradually introduced into the autoclave and reacted. Along with the introduction of propylene oxide, the temperature in the autoclave was raised. Cooling was applied as needed to keep the reaction temperature at 150° C. or less. After the reaction, the pressure was reduced at 150° C. to 10 mmHg mercury column or less to remove excess propylene oxide and a propylene glycol polymer occurring as a by-product. The pH was adjusted to a value of 6 to 7 by performing neutralization with acetic acid. The OH value of the obtained dipentaerythritol 6PO adduct was 567.

Subsequently, 594 g (1 mol) of the obtained propylene glycol-modified dipentaerythritol (OH value: 567), 562 g (7.8 mol) of acrylic acid, 58 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 771 g (yield: 84%) of dipentaerythritol 6PO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 6PO adduct acrylate. The results of NMR analysis and LC-MS analysis are shown below, and the attribution of peak of NMR is indicated by the above-described number.

<Dipentaerythritol 6PO Adduct Acrylate> ($^{13}$C-NMR Analysis (400 MHz), in CDCl3)

20 ppm: derived from propylene oxide, 45 ppm: derived from (2), 60 ppm: derived from (3), from 61 to 63 ppm: derived from (3) added with propylene oxide, from 65 to 80 ppm: derived from propylene oxide added to (3), from 77 to 79 ppm: derived from deuterated chloroform, from 128 to 131 ppm: derived from ester-bound acrylic acid, and from 165 to 167 ppm: ester bond moiety.

<Dipentaerythritol 6PO Adduct Acrylate> ($^1$H-NMR Analysis (400 MHz), in CDCl3)

1.4 ppm (18H): derived from methyl group of propylene oxide added to OH of (3), from 3.2 to 4.3 ppm (34H): derived from (1), (3) and propylene oxide (excluding methyl group) added to (3), from 5.7 to 6.5 ppm (18H): derived from acrylic acid ester-bound to propylene oxide added to (3), and 7.3 ppm: derived from deuterated chloroform.

<Dipentaerythritol 6PO Adduct Acrylate> (LC-MS Analysis)

From 14 to 15 minutes: dipentaerythritol pentaacrylate and dipentaerythritol hexaacrylate, from 16.1 to 23.2: dipentaerythritol propylene oxide-modified hexaacrylate, and from 15 to 20.1 minutes: poly(propylene oxide) diacrylate.

Example 10

(Synthesis of Dipentaerythritol 4BO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 2 g of KOH were charged, and the contents were subjected to a temperature rise to 90° C. with stirring to form a slurry-like liquid. The liquid was then heated to 150° C., and 360 g (5 mol) of butylene oxide was gradually introduced into the autoclave and reacted. Along with the introduction of butylene oxide, the temperature in the autoclave was raised. Cooling was applied as needed to keep the reaction temperature at 150° C. or less. After the reaction, the pressure was reduced at 150° C. to 10 mmHg mercury column or less to remove excess butylene oxide and a butylene glycol polymer occurring as a by-product. The pH was adjusted to a value of 6 to 7 by performing neutralization with acetic acid. The OH value of the obtained dipentaerythritol 4BO adduct was 660.

Subsequently, 510 g (1 mol) of the obtained butylene glycol-modified dipentaerythritol (OH value: 660), 562 g (7.8 mol) of acrylic acid, 51 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 701 g (yield: 84%) of dipentaerythritol 4BO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 4BO adduct acrylate. The results of NMR analysis and LC-MS analysis are shown below, and the attribution of peak of NMR is indicated by the above-described number.

<Dipentaerythritol 4BO Adduct Acrylate> ($^{13}$C-NMR Analysis (400 MHz), in CDCl3)

29 ppm: derived from butylene oxide, 45 ppm: derived from (2), 60 ppm: derived from (3), from 61 to 63 ppm: derived from (3) added with butylene oxide, 63 ppm: derived from butylene oxide added to (3), from 77 to 79 ppm: derived from deuterated chloroform, from 128 to 131 ppm: derived from ester-bound acrylic acid, and from 165 to 167 ppm: ester bond moiety.

<Dipentaerythritol 4BO Adduct Acrylate> ($^1$H-NMR Analysis (400 MHz), in CDCl3)

From 1.1 to 1.6 ppm (20H): derived from ethyl group of butylene oxide, from 3.3 to 4.3 ppm (28H): derived from (1), (3) and butylene oxide (excluding ethyl group) added to (3), from 5.5 to 6.5 ppm (18H): derived from (3) and acrylic acid ester bound to butylene oxide added to (3), and 7.3 ppm: derived from deuterated chloroform.

<Dipentaerythritol 4BO Adduct Acrylate> (LC-MS Analysis)

From 17.0 to 22.1 minutes: poly(butylene oxide) diacrylate, from 16.3 to 23.0: dipentaerythritol butylene oxide-modified pentaacrylate, and from 17 to 24 minutes: dipentaerythritol butylene oxide-modified hexaacrylate.

Example 11

(Synthesis of Dipentaerythritol 6BO Adduct Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 2 g of KOH were charged, and the contents were subjected to a temperature rise to 90° C. with stirring to form a slurry-like liquid. The liquid was then heated to 150° C., and 504 g (7 mol) of butylene oxide was gradually introduced into the autoclave and reacted. Along with the introduction of butylene oxide, the temperature in the autoclave was raised. Cooling was applied as needed to keep the reaction temperature at 150° C. or less. After the reaction, the pressure was reduced at 150° C. to 10 mmHg mercury column or less to remove excess butylene oxide and a butylene glycol polymer occurring as a by-product. The pH was adjusted to a value of 6 to 7 by performing neutralization with acetic acid. The OH value of the obtained dipentaerythritol 6BO adduct was 518.

Subsequently, 650 g (1 mol) of the obtained butylene glycol-modified dipentaerythritol (OH value: 518), 562 g (7.8 mol) of acrylic acid, 51 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 799 g (yield: 82%) of dipentaerythritol 4BO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 6BO adduct acrylate. The results of NMR analysis and LC-MS analysis are shown below, and the attribution of peak of NMR is indicated by the above-described number.

<Dipentaerythritol 6BO Adduct Acrylate> ($^{13}$C-NMR Analysis (400 MHz), in CDCl3)

29 ppm: derived from butylene oxide, 45 ppm: derived from (2), 60 ppm: derived from (3), from 61 to 63 ppm: derived from (3) added with butylene oxide, 63 ppm: derived from butylene oxide added to (3), from 77 to 79 ppm: derived from deuterated chloroform, from 128 to 131 ppm: derived from ester-bound acrylic acid, and from 165 to 167 ppm: ester bond moiety.

<Dipentaerythritol 6BO Adduct Acrylate> ($^1$H-NMR Analysis (400 MHz), in CDCl3)

From 1.1 to 1.6 ppm (30H): derived from ethyl group of butylene oxide, from 3.3 to 4.3 ppm (34H): derived from (1), (3) and butylene oxide (excluding ethyl group) added to (3), from 5.5 to 6.5 ppm (18H): derived from acrylic acid ester-bound to butylene oxide added to (3), and 7.3 ppm: derived from deuterated chloroform.

<Dipentaerythritol 6BO Adduct Acrylate> (LC-MS Analysis)

From 17.0 to 22.1 minutes: poly(butylene oxide) diacrylate, from 16.3 to 23.0: dipentaerythritol butylene oxide-modified pentaacrylate, and from 17 to 24 minutes: dipentaerythritol butylene oxide-modified hexaacrylate.

Example 12

(Synthesis of Dipentaerythritol 4EO Adduct Acrylate Increased in Amount of By-Product Poly(Ethylene Oxide) Acrylate)

Into a 1 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated to 130° C., and 242 g (5.5 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 20 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 4EO adduct was 775.

Subsequently, 434 g (1 mol) of the obtained ethylene glycol-modified dipentaerythritol (OH value: 775), 562 g (7.8 mol) of acrylic acid, 50 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 637 g (yield: 84%) of dipentaerythritol 4EO adduct acrylate represented by the formula (1).

With respect to this product, measurement of hydroxyl value and analyses by $^1$H-NMR, $^{13}$C-NMR, HPLC and LC-MS were performed. As a result, the compound obtained was revealed to be dipentaerythritol 4EO adduct acrylate. The results of NMR analysis and LC-MS analysis are shown below, and the attribution of peak of NMR is indicated by the above-described number.

<Dipentaerythritol 4EO Adduct Acrylate Increased in Amount of By-Product Poly(Ethylene Oxide) Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bound acrylic acid, and from 165 to 167 ppm: ester bond moiety.

<Dipentaerythritol 4EO Adduct Acrylate Increased in Amount of By-Product Poly(Ethylene Oxide) Acrylate> ($^1$H-NMR Analysis (400 MHz), in CDCl3)

From 3.3 to 4.1 ppm (16H): derived from (1) and (3), from 3.6 to 4.4 ppm (16H): derived from ethylene oxide added to OH of (3), from 5.7 to 6.4 ppm (18H): derived from double bond of acrylic acid ester, and 7.3 ppm: derived from deuterated chloroform.

<Dipentaerythritol 4EO Adduct Acrylate Increased in Amount of By-Product Poly(Ethylene Oxide) Acrylate> (LC-MS Analysis)

From 8.8 to 11.5 minutes: poly(ethylene oxide) diacrylate, from 14 to 16 minutes: dipentaerythritol ethylene oxide-modified monoacrylate, and from 16 to 20 minutes: dipentaerythritol ethylene oxide-modified hexaacrylate.

Comparative Example 1

(Synthesis of Dipentaerythritol 12EO Adduct Acrylate)

Into a 2 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 572 g (13 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 12EO adduct was 434.

Subsequently, 776 g (1 mol) of the obtained ethylene glycol-modified dipentaerythritol (OH value: 434), 562 g (7.8 mol) of acrylic acid, 50 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 902 g (yield: 82%) of dipentaerythritol 4EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 12EO adduct acrylate. The results of NMR analysis and LC-MS analysis are shown below, and the attribution of peak of NMR is indicated by the above-described number.

<Dipentaerythritol 12EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 68 to 73 ppm: derived from ethylene oxide added to (3), from 77 to 79 ppm: derived from deuterated chloroform, from 128 to 131 ppm: derived from ester-bound acrylic acid, and from 165 to 167 ppm: ester bond moiety.

<Dipentaerythritol 12EO Adduct Acrylate> ($^1$H-NMR Analysis (400 MHz), in CDCl3)

From 3.3 to 4.1 ppm (16H): derived from (1) and (3), from 3.6 to 4.4 ppm (48H): derived from ethylene oxide added to OH of (3), from 5.7 to 6.4 ppm (18H): derived from double bond of acrylic acid ester, and 7.3 ppm: derived from deuterated chloroform.

<Dipentaerythritol 12EO Adduct Acrylate> (LC-MS Analysis)

From 8.8 to 12.1 minutes: poly(ethylene oxide) diacrylate, from 14 to 16 minutes: dipentaerythritol ethylene oxide-modified monoacrylate, and from 16 to 21 minutes: dipentaerythritol ethylene oxide-modified hexaacrylate.

Comparative Example 2

(Synthesis of Dipentaerythritol 30EO Adduct Acrylate)

Into a 2 L-volume autoclave equipped with a stirring device, 254 g (1.0 mol) of dipentaerythritol (produced by Koei Chemical Co., Ltd., OH value: 1,324), 127 g of toluene and 0.3 g of KOH were charged, and the contents were subjected to a temperature rise to 90° C. with stirring to form a slurry-like liquid. The liquid was then heated at 130° C., and 1,364 g (31 mol) of ethylene oxide was gradually introduced into the autoclave and reacted. Along with the introduction of ethylene oxide, the temperature in the autoclave was raised. Cooling was applied as needed to keep the reaction temperature at 140° C. or less. After the reaction, the pressure was reduced at 140° C. to 10 mmHg mercury column or less to remove excess ethylene oxide and an ethylene glycol polymer occurring as a by-product. Thereafter, the pH was adjusted to a value of 6 to 7 by performing neutralization with acetic acid. The OH value of the obtained dipentaerythritol 30EO adduct was 215.

Subsequently, 1,290 g (1 mol) of the obtained ethylene glycol-modified dipentaerythritol (OH value: 215), 562 g (7.8 mol) of acrylic acid, 50 g of para-toluenesulfonic acid, 900 g of toluene and 1 g of hydroquinone were charged into a glass-made four-neck flask, and a thermal reaction was performed with blowing air into the flask. The water produced by the reaction was removed out of the system by azeotroping with toluene as needed. The reaction temperature was from 100 to 110° C., and the amount of reaction water removed out of the system at the completion of reaction was 113 g. After the reaction, aqueous alkali washing and water washing were preformed to separate the upper-layer toluene layer, and the toluene was removed by distillation under reduced pressure to obtain 1,258 g (yield: 78%) of dipentaerythritol 30EO adduct acrylate represented by the formula (I).

With respect to this product, measurement of hydroxyl value and analyses by $^1$H-NMR, $^{13}$C-NMR, HPLC and LC-MS were performed. As a result, the compound obtained was revealed to be dipentaerythritol 30EO adduct acrylate. The results of NMR analysis and LC-MS analysis are shown below, and the attribution of peak of NMR is indicated by the above-described number.

<Dipentaerythritol 30EO Adduct Acrylate> ($^{13}$C-NMR Analysis (400 MHz), in CDCl3)

45 ppm: derived from (2), 60 ppm: derived from (3), from 61 to 63 ppm: derived from (3) added with ethylene oxide, from 67 to 74 ppm: derived from ethylene oxide added to (3), from 77 to 79 ppm: derived from deuterated chloroform, from 128 to 131 ppm: derived from ester-bonded acrylic acid, and from 165 to 167 ppm: ester bond moiety.

<Dipentaerythritol 30EO Adduct Acrylate> ($^1$H-NMR Analysis (400 MHz), in CDCl3)

From 3.3 to 4.1 ppm (16H): derived from (1) and (3), from 3.6 to 4.4 ppm (120H): derived from ethylene oxide added to OH of (3), from 5.7 to 6.4 ppm (18H): derived from double bond of acrylic acid ester, and 7.3 ppm: derived from deuterated chloroform.

<Dipentaerythritol 30EO Adduct Acrylate> (LC-MS Analysis)

From 8.8 to 12.5 minutes: poly(ethylene oxide) diacrylate, and from 16 to 24 minutes: dipentaerythritol ethylene oxide-modified hexaacrylate.

Comparative Example 3

(AO-unmodified Dipentaerythritol Acrylate)

As a target for comparison with the AO-modified dipentaerythritol acrylate of the present invention, an AO-unmodified dipentaerythritol, KAYARAD DPHA (dipentaerythritol pentalhexaacrylate mixture, hereinafter simply referred to as DPHA), produced by Nippon Kayaku Co., Ltd. was used.

The samples obtained in Examples and Comparative Examples above were evaluated by the following methods. The results are shown in Table 1.

[Viscosity]

The viscosity was measured in accordance with JIS K 5600-2-3.

[Photosensitivity]

A material obtained by adding and dissolving 50 parts by weight of the sample obtained in each of Examples 1 to 14 and Comparative Examples, 50 parts by weight of ethyl acetate, and irgacure 184 produced by BASF as a photopolymerization initiator in an amount of 3 parts by weight based on the solid matters was coated on a glass substrate by a spin coater to a dry thickness of 5 μm and dried at 80° C. to remove the solvent. This uncured product was cured at an integrated illuminance of 200 mj in a nitrogen atmosphere by using a parallel light exposure system (SX-UID501H UVQ) manufactured by Ushio Inc. with blocking light through a step tablet (25 steps, manufactured by Riston), and the step number when the touch by a finger becomes tack-free is shown.

[Polymerization Ratio]

A sample prepared in the same manner as in the item of photosensitivity was coated on a steel plate to a dry thickness of 5 μm and dried at 80° C. to remove the solvent. This test piece was cured at an integrated illuminance of 200 mj and 1,000 mj under the same conditions as in the item of photosensitivity. After measuring the test piece by ATR-IR method, the ester bond-derived peak near 1,740 $cm^{-1}$ and the double bond-derived peak near 810 $cm^{-1}$ were compared, and the correlation between the disappearance of peak near 810 $cm^{-1}$ and the integrated illuminance was confirmed to thereby ascertain the curability.

[Adherence]

A sample prepared in the same manner as in the item of photosensitivity was cured at an integrated illuminance of 200 mj/$cm^2$ on ABS, acrylic resin and PC substrates by using a belt conveyer-type UV curing apparatus fitted with a metal halide lamp and after performing a cross-cut test specified in JIS-K5400, the number of remaining squares was taken as the adherence.

[Pencil Hardness]

A cured film was formed by the same technique as in the adherence test, and the film hardness on ABS, PC, PET and acrylic resin was measured in accordance with JIS K5600-5-4.

[Abrasion Resistance]

A cured film was formed on a PET substrate by the same technique as in the adherence test and subjected to the Taber abrasion test. The haze after a predetermined number of cycles using a CS-10F abrasion wheel loaded with 500 g was measured by a haze meter (Model HGM, manufactured by Suga Test Instruments Co., Ltd.), and a haze difference between before and after the test was determined.

[Steel Wool Resistance]

A cured film was formed on a PET substrate by the same technique as in the adherence test, and the state of coating film after polishing 100 times with #00 steel wool under a load of 3 kg was observed with an eye and evaluated according to the following criteria:

A: no scratch, B: around 10 scratches could be confirmed on the test piece, and C: many scratches could be confirmed.

[Curling Property]

A 150 μm-thick PET film cut into a square 6 cm on a side was used as the base material, and a cured film was formed thereon by the same technique as in the adherence test. Out of four corners of the film, one point was fixed to a flat surface and at this time, the heights of the remaining three points were measured. The average value thereof was taken as the curling property.

[Contamination Resistance]

A cured film was formed on a PET substrate by the same technique as in the adherence test. A permanent marker, a hair dye liquid or a shoe polish was coated as a contaminant on the cured film and the film was left standing still for 18 hours and wiped off with ethanol-impregnated cotton. The outer appearance was observed with an eye and evaluated according to the following criteria:

A: no coloring, B: slightly colored, and C: deeply colored.

[Acid Resistance]

A cured film was formed by the same technique as in the adherence test, and one drop of an aqueous 0.1 mol/L hydrochloric acid solution was dropped on the test film, left standing still for 18 hours in a petri dish, and wiped off with tissue paper. Whether the film was changed or not was observed with an eye and evaluated according to the following criteria:

A: no abnormality on the cured film, B: a slight change in gloss was observed, and C: an obvious abnormality such as whitening, cracking or floating was observed on the cured film.

[Alkali Resistance]

A cured film was formed by the same technique as in the adherence test, and one drop of an aqueous 2% sodium hydroxide solution was dropped on the test film, left standing still for 18 hours in a petri dish, and wiped off with tissue paper. Whether the film was changed or not was observed with an eye and evaluated according to the following criteria:

A: no abnormality on the cured film, B: a slight change in gloss was observed, and C: an obvious abnormality such as whitening, cracking or floating was observed on the cured film.

[Water Resistance]

A cured film was formed by the same technique as in the adherence test, and the outer appearance when tap water was dropped thereon and after 18 hours, wiped off was observed with an eye and evaluated according to the following criteria:

A: no abnormality on the cured film, B: a slight change in gloss was observed, and C: an obvious abnormality such as whitening, cracking or floating was observed on the cured film.

[Chemical Resistance]

A cured film was formed by the same technique as in the adherence test, and a commercially available bleach consisting of hypochlorite, sodium hydroxide, a surfactant (alkylamine oxide), etc. was dropped on the test film, left standing still for 18 hours in a petri dish, and wiped off with tissue paper. Whether the film was changed or not was observed with an eye and evaluated in the same manner as the water resistance.

[Contact Angle]

This was measured by a drop method. The height of apex and the radius of droplet were directly read, and the contact angle was determined according to θ=2 arctan (h/a). The contact angles after 0.2 seconds and after 5 seconds were measured.

[Crystallinity]

20 ml of the sample was put into a 100-ml glass-made screw-top bottle and stored in a refrigerator at 0° C. for 3 months, and the presence or absence of crystallization was observed with an eye and evaluated according to the following criteria:

A: liquid form, B: slurry form, and C: crystallized.

TABLE 1

| Sample | Viscosity m·pa·s/25° C. | Photosensitivity x/25 | Polymerization Ratio | | LC-MS Measurement By-Product |
|---|---|---|---|---|---|
| | | | After Irradiation at 200 mj (%) | After Irradiation at 1000 mj (%) | Poly(alkylene Oxide) Acrylate |
| Example 1 (dipentaerythritol 2EO adduct acrylate) | 1700 | 7 | 73.3 | 86.4 | 3.0 |
| Example 2 (dipentaerythritol 3EO adduct acrylate) | 910 | 8 | 73.2 | 86.6 | 4.5 |
| Example 3 (dipentaerythritol 3.5EO adduct acrylate) | 770 | 9 | 79.5 | 91.3 | 3.5 |
| Example 4 (dipentaerythritol 4EO adduct acrylate) | 393 | 12 | 85.1 | 92.8 | 11.5 |
| Example 5 (dipentaerythritol 5EO adduct acrylate) | 635 | 11 | 84.2 | 92.1 | 3.6 |
| Example 6 (dipentaerythritol 6EO adduct acrylate) | 567 | 11 | 85.3 | 92.3 | 0.6 |
| Example 7 (dipentaerythritol 4EO adduct acrylate reduced in amount of by-product poly(ethylene oxide) acrylate) | 501 | 12 | 84.0 | 90.7 | 1.1 |
| Example 8 (dipentaerythritol 4PO adduct acrylate) | 1600 | 6 | 83.8 | 91.2 | 2.1 |
| Example 9 (dipentaerythritol 6PO adduct acrylate) | 1024 | 7 | 86.9 | 92.6 | 2.3 |
| Example 10 (dipentaerythritol 4BO adduct acrylate) | 2100 | 7 | 81.5 | 88.0 | 1.8 |
| Example 11 (dipentaerythritol 6BO adduct acrylate) | 1880 | 8 | 83.2 | 89.2 | 3.4 |
| Example 12 (dipentaerythritol 4EO adduct acrylate increased in amount of by-product poly(ethylene oxide) acrylate) | 349 | 12 | 83.1 | 90.4 | 18.0 |
| Comparative Example 1 (dipentaerythritol 12EO adduct acrylate) | 570 | 12 | 87.4 | 91.2 | 4.4 |
| Comparative Example 2 (dipentaerythritol 30EO adduct acrylate) | 680 | 12 | 87.7 | 91.9 | 6.1 |
| Comparative Example 3 (AO-unmodified dipentaerythritol acrylate) | 7200 | 4 | 58.9 | 74.4 | 0.0 |

| Sample | Adherence | | | Pencil Hardness | | | | Abrasion Resistance | Steel Wool Resistance |
|---|---|---|---|---|---|---|---|---|---|
| | ABS | PC | Acrylic Plate | ABS | PC | PET | Acrylic Plate | | |
| Example 1 (dipentaerythritol 2EO adduct acrylate) | 100/100 | 100/100 | 100/100 | HB | F | 4H | 5H | 3.3 | A |
| Example 2 (dipentaerythritol 3EO adduct acrylate) | 100/100 | 100/100 | 100/100 | HB | F | 4H | 5H | 3.1 | A |
| Example 3 (dipentaerythritol 3.5EO adduct acrylate) | 100/100 | 100/100 | 100/100 | HB | F | 4H | 4H | 4.4 | A |
| Example 4 (dipentaerythritol 4EO adduct acrylate) | 100/100 | 100/100 | 100/100 | HB | F | 4H | 4H | 4.0 | A |
| Example 5 (dipentaerythritol 5EO adduct acrylate) | 100/100 | 100/100 | 100/100 | HB | F | 4H | 4H | 5.1 | A |
| Example 6 (dipentaerythritol 6EO adduct acrylate) | 100/100 | 100/100 | 100/100 | B | HB | 3H | 3H | 5.0 | A |
| Example 7 (dipentaerythritol 4EO adduct acrylate reduced in amount of by-product poly(ethylene oxide) acrylate) | 100/100 | 100/100 | 100/100 | HB | F | 4H | 4H | 3.8 | A |
| Example 8 (dipentaerythritol 4PO adduct acrylate) | 100/100 | 100/100 | 100/100 | B | HB | 2H | 3H | 5.9 | B |
| Example 9 (dipentaerythritol 6PO adduct acrylate) | 100/100 | 100/100 | 100/100 | B | HB | 2H | 3H | 6.6 | B |
| Example 10 (dipentaerythritol 4BO adduct acrylate) | 100/100 | 100/100 | 100/100 | 2B | B | H | 2H | 6.3 | B |
| Example 11 (dipentaerythritol 6BO adduct acrylate) | 100/100 | 100/100 | 100/100 | 2B | B | H | 2H | 7.2 | B |
| Example 12 (dipentaerythritol 4EO adduct acrylate increased in amount of by-product poly(ethylene oxide) acrylate) | 100/100 | 100/100 | 100/100 | B | HB | 3H | 3H | 6.5 | B |
| Comparative Example 1 (dipentaerythritol 12EO adduct acrylate) | 100/100 | 100/100 | 100/100 | 2B | B | H | H | 8.8 | B |
| Comparative Example 2 (dipentaerythritol 30EO adduct acrylate) | 100/100 | 100/100 | 100/100 | 3B | 3B | B | B | 16 | C |
| Comparative Example 3 (AO-unmodified dipentaerythritol acrylate) | 100/100 | 100/100 | 100/100 | HB | F | 4H | 5H | 2.3 | A |

| Sample | Curling Property | Contamination Resistance | | | Acid Resistance | Alkali Resistance |
|---|---|---|---|---|---|---|
| | | Permanent Marker | Hair Dye Liquid | Shoe Polish | | |
| Example 1 (dipentaerythritol 2EO adduct acrylate) | 7.4 | A | A | A | A | A |
| Example 2 (dipentaerythritol 3EO adduct acrylate) | 6.2 | A | A | A | A | A |
| Example 3 (dipentaerythritol 3.5EO adduct acrylate) | 5.1 | A | A | A | A | A |
| Example 4 (dipentaerythritol 4EO adduct acrylate) | 2.1 | A | A | A | A | A |
| Example 5 (dipentaerythritol 5EO adduct acrylate) | 3.6 | A | A | A | A | A |
| Example 6 (dipentaerythritol 6EO adduct acrylate) | 3.5 | A | A | A | A | A |

TABLE 1-continued

| Example 7 (dipentaerythritol 4EO adduct acrylate reduced in amount of by-product poly(ethylene oxide) acrylate) | 6.2 | A | A | A | A | A |
|---|---|---|---|---|---|---|
| Example 8 (dipentaerythritol 4PO adduct acrylate) | 5.9 | A | A | A | A | A |
| Example 9 (dipentaerythritol 6PO adduct acrylate) | 5.3 | B | B | B | B | B |
| Example 10 (dipentaerythritol 4BO adduct acrylate) | 6.2 | A | A | A | A | A |
| Example 11 (dipentaerythritol 6BO adduct acrylate) | 5.4 | B | B | B | B | B |
| Example 12 (dipentaerythritol 4EO adduct acrylate increased in amount of by-product poly(ethylene oxide) acrylate) | 2.3 | B | B | B | B | B |
| Comparative Example 1 (dipentaerythritol 12EO adduct acrylate) | 2.0 | B | B | B | B | B |
| Comparative Example 2 (dipentaerythritol 30EO adduct acrylate) | 1.3 | B | C | A | C | C |
| Comparative Example 3 (AO-unmodified dipentaerythritol acrylate) | 8.2 | A | A | A | A | A |

| Sample | Water Resistance | Chemical Resistance | Contact Angle After 0.2 sec | Contact Angle After 5 sec | Crystallinity |
|---|---|---|---|---|---|
| Example 1 (dipentaerythritol 2EO adduct acrylate) | A | A | 56.7 | 56.3 | B |
| Example 2 (dipentaerythritol 3EO adduct acrylate) | A | A | 56.6 | 56.1 | A |
| Example 3 (dipentaerythritol 3.5EO adduct acrylate) | A | A | 55.8 | 53.0 | A |
| Example 4 (dipentaerythritol 4EO adduct acrylate) | A | A | 55.0 | 52.1 | A |
| Example 5 (dipentaerythritol 5EO adduct acrylate) | A | A | 54.6 | 51.8 | A |
| Example 6 (dipentaerythritol 6EO adduct acrylate) | A | A | 54.0 | 51.1 | A |
| Example 7 (dipentaerythritol 4EO adduct acrylate reduced in amount of by-product poly(ethylene oxide) acrylate) | A | A | 55.3 | 52.5 | A |
| Example 8 (dipentaerythritol 4PO adduct acrylate) | A | A | 57.1 | 55.4 | A |
| Example 9 (dipentaerythritol 6PO adduct acrylate) | B | B | 56.3 | 54.2 | A |
| Example 10 (dipentaerythritol 4BO adduct acrylate) | A | A | 57.9 | 56.5 | A |
| Example 11 (dipentaerythritol 6BO adduct acrylate) | B | B | 58.7 | 57.0 | B |
| Example 12 (dipentaerythritol 4EO adduct acrylate increased in amount of by-product poly(ethylene oxide) acrylate) | B | B | 54.0 | 51.1 | A |
| Comparative Example 1 (dipentaerythritol 12EO adduct acrylate) | B | B | 39.5 | 19.7 | A |
| Comparative Example 2 (dipentaerythritol 30EO adduct acrylate) | B | C | 35.6 | 17.9 | A |
| Comparative Example 3 (AO-unmodified dipentaerythritol acrylate) | A | A | 57.0 | 56.7 | C |

As seen from the results in Table 1, with respect to high viscosity that has been a conventional problem, the viscosity can be greatly reduced by AO modification of dipentaerythritol (meth)acrylate. In addition, since the viscosity is also changed by the amount of by-product poly(alkylene oxide) (meth)acrylate, the desired product viscosity can be obtained by controlling the amount of by-product poly(alkylene oxide) (meth)acrylate contained.

As for photosensitivity, enhancement of the photosensitivity was confirmed in any of modifications with ethylene oxide, propylene oxide and butylene oxide. High photosensitivity was exhibited in the ethylene oxide modification, and highest photosensitivity was exhibited when the addition mol number is around 4.

It is seen that the polymerization ratio is also greatly enhanced by AO modification, and among others, in the ethylene oxide modification, a highest polymerization ratio is exhibited when the addition mol number is around 4.

As seen from the measurement results of the amount of by-product poly(alkylene oxide) (meth)acrylate by LC-MS analysis shown in Table 1, the amount of by-product poly(alkylene oxide) (meth)acrylate is increased, in order, in Examples 7, 4 and 12 and the viscosity is decreased in that order, which leads to an understanding that the viscosity can be controlled by controlling the amount of by-product poly(alkylene oxide) (meth)acrylate. In addition, it is seen that although a difference is not observed in the photosensitivity by a finger touch test, the polymerization ratio is increased by containing a certain amount of by-product poly(alkylene oxide) (meth)acrylate as in Example 4 and is decreased when the amount is too large as in Example 12. This is considered that since a by-product poly(alkylene oxide) (meth)acrylate interpolates between (meth)acryloyl groups of the alkylene oxide-modified dipentaerythritol (meth)acrylate, a closest-packed state is thereby created. Other physical properties of the cured film tend to be deteriorated as the amount of by-product poly(alkylene oxide) (meth)acrylate is increased, and it is understood that various physical properties can be adjusted by controlling the amount of by-product poly(alkylene oxide) (meth)acrylate.

As confirmed from Table 1, the adherence is not decreased depending on the kind or addition mol number of alkylene oxide. The pencil hardness of the cured film is found to decrease in order of ethylene oxide, propylene oxide and butylene oxide and in the same structure, is decreased as the addition mol number is increased. This is attributable mainly to reduction in the crosslinking density and is also true for other evaluation items of abrasion resistance, steel wool resistance, contamination resistance, acid resistance, alkali resistance, water resistance and chemical resistance. As for the crystallinity, it is found that the crystallinity of the acrylate of dipentaerythritol can be reduced by alkylene oxide modification. However, in the modification with a linear skeleton having high crystallinity like butylene oxide of Example 12, reduction in the crystallinity is insufficient.

Also, as understood from comparison among Examples 4, 7 and 12, the amount of by-product poly(alkylene oxide) (meth)acrylate is correlated with the contact angle of the cured film.

INDUSTRIAL APPLICABILITY

As described in the above, the composition containing an alkylene oxide-modified dipentaerythritol (meth)acrylate compound represented by the formula (I) of the present invention, in which the AO addition mol number is optimized and the content of by-product alkylene oxide is controlled, exhibits excellent photosensitivity, low crystallinity and low viscosity leading to excellent dilutability and provides a cured product with low cure shrinkage and high hardness, so that a polymerizable resin composition where a (meth)acrylate of a polyfunctional alcohol represented by dipentaerythritol, pentaerythritol, ditrimethylolpropane, trimethylolpropane, pentaerythritol and the like has been blended can be more decreased in the viscosity and the physical properties of the cured product can be enhanced. Accordingly, this composition can be suitably used for applications, e.g., a resist resin composition such as dry film resist, color resist, black resist and semiconductor resist, a resin composition for medical use such as dental use, a resin composition for paint/coating, an ink composition for printing, a film coating, a black matrix, a photospacer etc.

The invention claimed is:

1. A reactive composition containing an ethylene oxide-modified dipentaerythritol acrylate and a poly(ethylene oxide) acrylate, wherein said ethylene oxide-modified dipentaerythritol acrylate has a structure represented by formula (I)

$$\left[ \begin{array}{c} -O- \\ \diagdown_O \diagup \\ -O- \end{array} \diagdown O \diagup \begin{array}{c} -O- \\ \diagdown O \diagup \\ -O- \end{array} \left[ \begin{array}{c} -(AO)_{(l)}-R \\ -H_{(n)} \\ -R_{(o)} \end{array} \right]_{(m)} \right] \qquad (I)$$

wherein,

R represents a substituent represented by the formula (II), wherein $R^2$ represents a hydrogen atom, $$R = \underset{R^2}{\overset{O}{\diagdown}} \qquad (II)$$

AO represents —$CH_2CH_2O$—;

l is average degree of polymerization of the added ethylene oxide and the average value is from 2 to 5;

average value of m is from 2 to 5;

n is 0;

average value of o is from 1 to 4;

the total value of m, n and o is 6; and wherein the content of said ethylene oxide-modified dipentaerythritol acrylate is 88.5% by mass or more and 98.9% by mass or less, and the content of the poly(ethylene oxide) acrylate is 1.1% by mass or more and 11.5% by mass or less, and wherein the ethylene oxide of the poly(ethylene oxide) acrylate has an average degree of polymerization of from 2 to 5.

* * * * *